United States Patent [19]
Melde

[11] Patent Number: 5,531,596
[45] Date of Patent: Jul. 2, 1996

[54] DENTAL HAND PIECE WITH WATER DISTRIBUTION SYSTEM

[76] Inventor: Chris R. Melde, 10029 N. 60th Pl., Scottsdale, Ariz. 85253

[21] Appl. No.: 450,416

[22] Filed: May 25, 1995

[51] Int. Cl.⁶ .................................................. A61C 1/02
[52] U.S. Cl. .............................. 433/104; 433/82; 433/115
[58] Field of Search .......................... 433/82, 100, 105, 433/115, 165

[56] References Cited

U.S. PATENT DOCUMENTS 3,136,059   6/1964   Nelson ........................................ 433/82

*Primary Examiner*—Cary E. O'Connor
*Attorney, Agent, or Firm*—H. Gordon Shields

[57] ABSTRACT

A dental hand piece includes a head to which is secured a burr, and a liquid supply or distribution assembly directs a stream of cooling liquid directly to the burr from exteriorly of the dental hand piece itself. The liquid supply assembly is connected to the head of the hand piece through a block, and the burr is hollow to connect directly to the liquid supply or distribution assembly through the block.

27 Claims, 5 Drawing Sheets

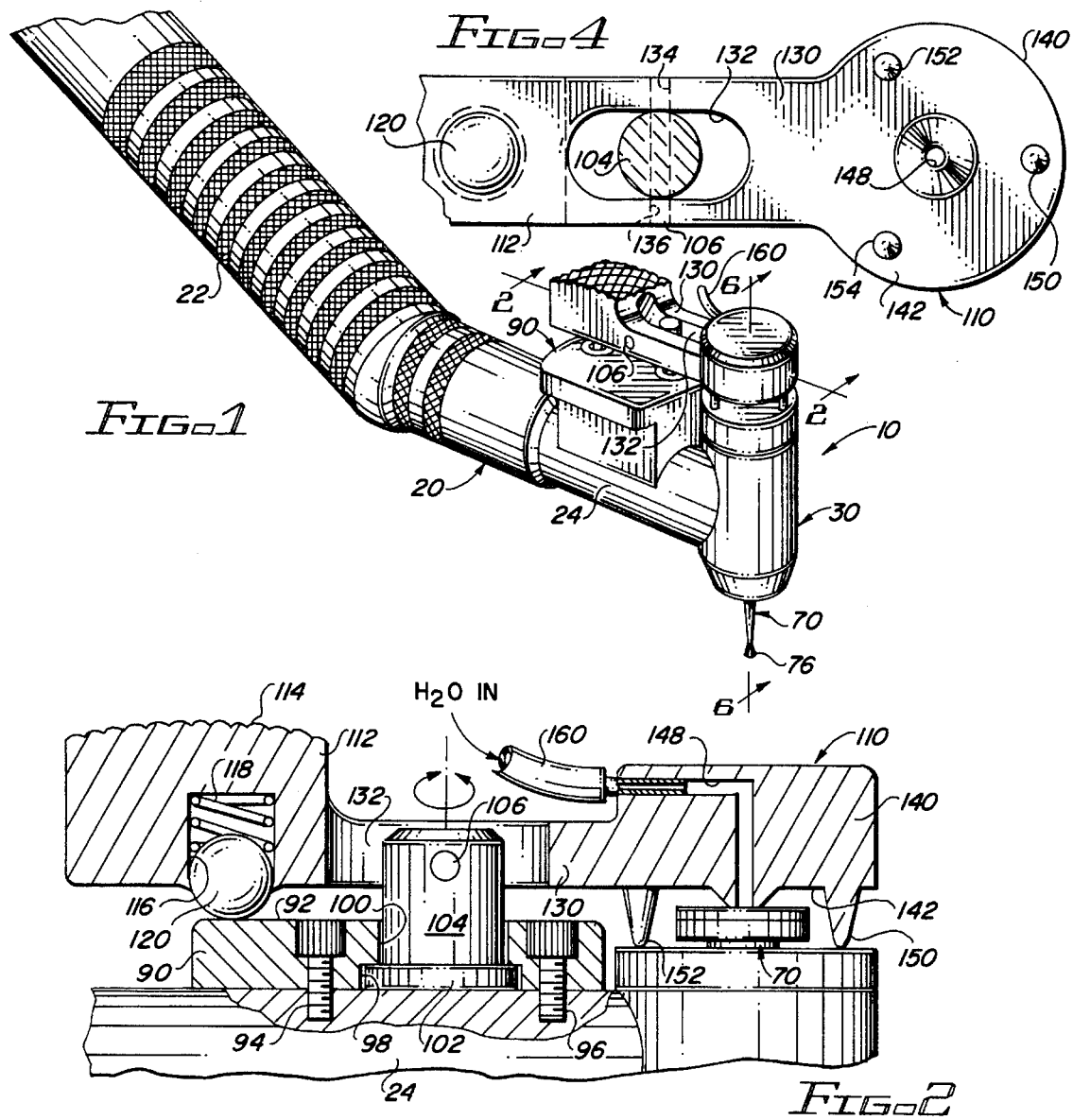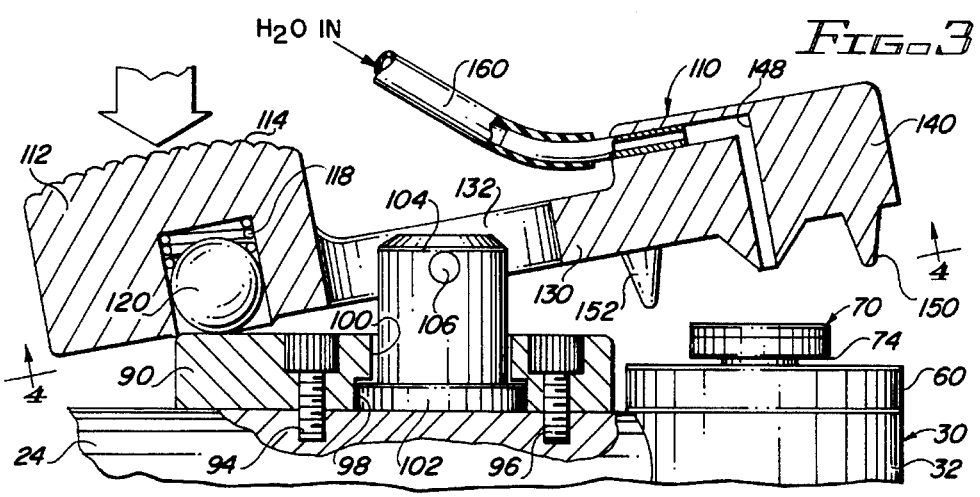

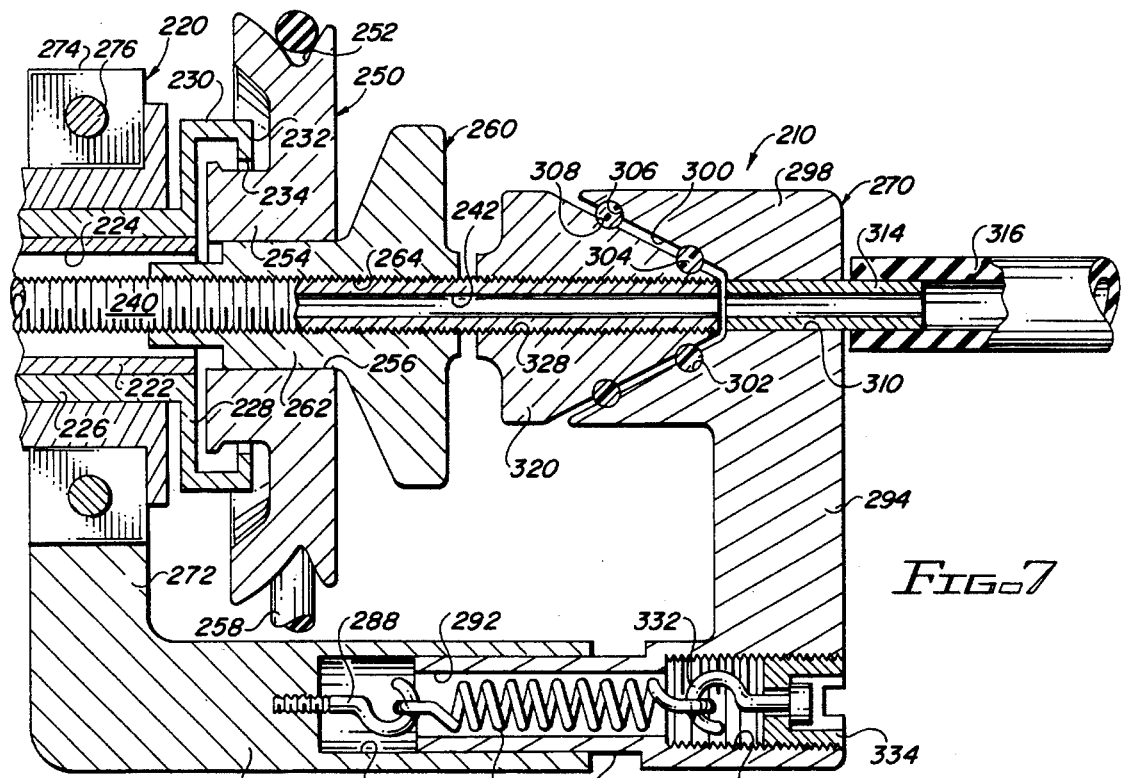
FIG-7
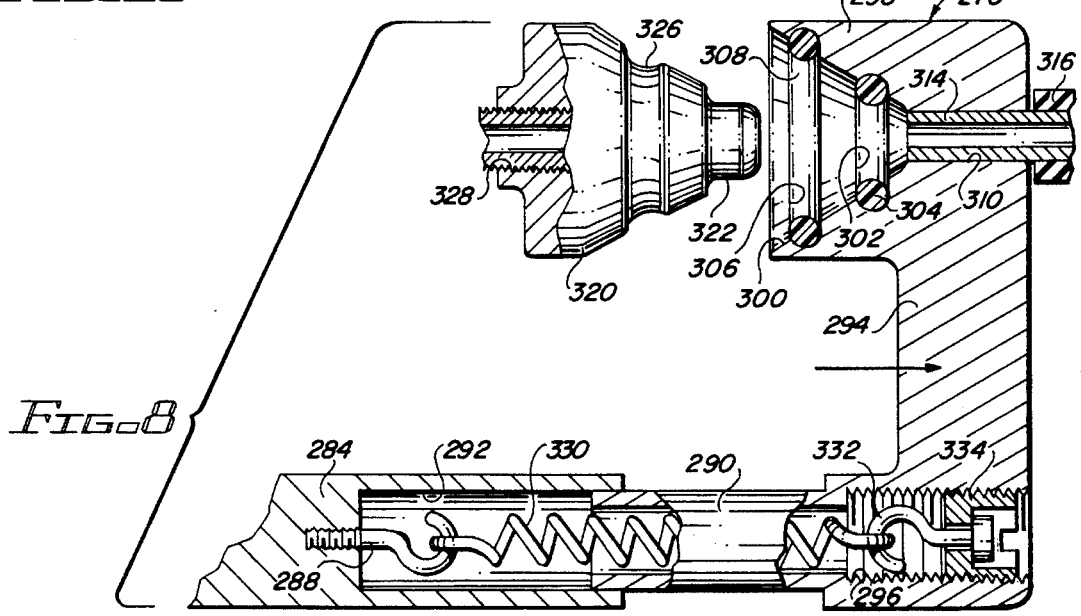
FIG-10
FIG-8

DENTAL HAND PIECE WITH WATER DISTRIBUTION SYSTEM

BACKGROUND OF THE INVENTION

1. Field of the Invention

This invention relates to dental drills and, more particularly, to dental drills which include a water distribution system for cooling purposes.

2. Description of the Prior Art

As dental drills have increased in their rotating speed, the heat caused by the friction of the high rotating speed on the teeth being worked on has required a coolant. Typically, water is used as a coolant. Typically, the water is conveyed through the dental hand piece, and specifically through the head of the hand piece. However, water droplets in high speed drills act like abrasives and cause problems with the drill, and with the various elements involved in the drill.

An example of the prior art is U.S. Pat. No. 3,762,052, the inventor of which is the inventor of the apparatus herein. In the '052 patent, water is introduced through the drill and through the burr. A combination of air pressure in centrifugal force helps to prevent water particles from entering into the bearings and other elements within the drill. However, while the '052 apparatus is an improvement over the prior art, it is still not completely effective in preventing water droplets from impinging on movable surfaces in the drill or hand piece head and of accordingly causing problems.

U.S. Pat. No. 3,778,904, the inventer of which is also the inventor herein, discloses another cooling system for dental hand piece. The '904 apparatus utilizes a stream of air as a coolant fluid, rather than water.

U.S. Pat. No. 3,871,097, the inventor of which is also the inventor of the present invention, is another improvement over the prior art. The '097 patent is a continuation-in-part of the '904 patent, and it similarly uses air as a cooling fluid.

The apparatus of the present invention utilizes water as a coolant fluid, and the water is conveyed to the drill apparatus externally of the drill itself. Water is conveyed externally of the hand piece directly to the burr of the hand piece, and the coolant water is hence delivered directly to the burr.

SUMMARY OF THE INVENTION

The invention described and claimed herein comprises a dental hand piece which utilizes a stream of water as a coolant fluid for cooling a burr in the dental hand piece. The coolant water system is delivered directly to the burr from exterior elements secured to the hand piece, rather than through the hand piece. The water supply system is secured to the head of the hand piece for delivering the stream of cooling water directly to and through the burr. The head of the hand piece is configured to allow a direct connection between the burr and the water supply elements. The water supply elements are coupled to the head of the hand piece with an adjustable tension system, and, in one embodiment, with appropriate o-ring sealing elements to prevent water droplets or particles from the coolant system from leaving the water supply and burr system and from entering into other elements of the head of the hand piece. In another embodiment, primarily for high speed air powered drills, air from a turbine is used to prevent water from entering into sensitive areas of the hand piece.

Among the objects of the present invention are the following:

To provide new and useful dental drill apparatus;

To provide new and useful dental drill apparatus utilizing water as a cooling medium;

To provide a new and useful dental burr having an axially extending bore for receiving a flow of cooling water;

To provide a new and useful dental burr having a replaceable cap;

To provide new and useful water supply system for a dental hand piece;

To provide new and useful water supply system for a burr in a dental hand piece; and To provide new and useful dental hand piece having a water supply system adjustably connected to the head of the dental hand piece.

BRIEF DESCRIPTION OF THE DRAWING

FIG. 1 is a perspective view of the apparatus of the present invention.

FIG. 2 is a view in partial section taken generally along line 2—2 of FIG. 1.

FIG. 3 is a view in partial section illustrating part of the operation of the apparatus illustrated in FIG. 2.

FIG. 4 is a view taken generally along line 4—4 of FIG. 3.

FIG. 7 is a view in partial section through an alternate embodiment of the apparatus of the present invention.

FIG. 8 is a view in partial section of a portion of the apparatus of FIG. 7.

FIG. 10 is a view in partial section of an alternate embodiment of a portion of the apparatus of FIG. 7.

DESCRIPTION OF THE PREFERRED EMBODIMENT

Figure 5:
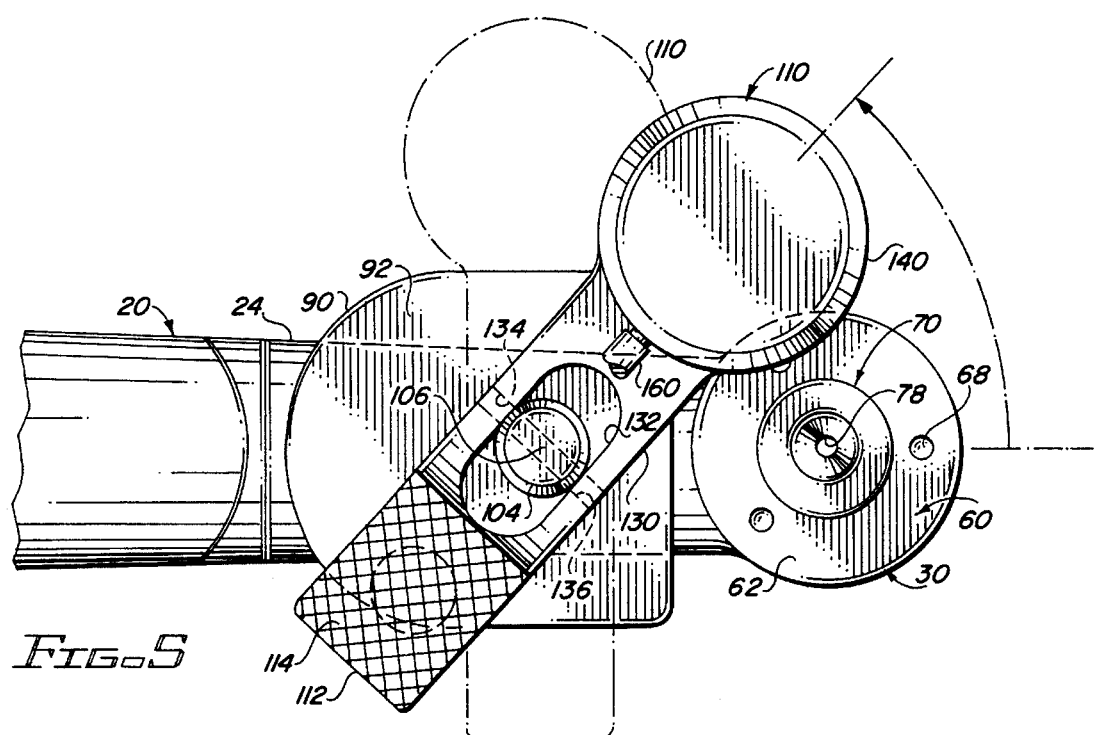
FIG. 5 is a top view of a portion of the apparatus of the present invention.

FIG. 1 is a perspective view of high speed dental drill apparatus 10 of the present invention. The drill apparatus 10 includes a hand piece 20 to which is secured a head 30. The hand piece 20 includes a generally hollow shank portion 22, and a handle 24. The head 30 is secured to the handle 24. A hollow burr 70 is secured to the head 30 and extends downwardly therefrom. The burr 70 includes a tip 76 appropriately configured for drilling in a tooth.

Secured to the upper portion of the hand piece 20 is a block 90. Disposed above the block 90 is a water distribution assembly 110.

FIG. 2 is a view in partial section of a portion of the apparatus 10 taken generally along line 2—2. A portion of the block 90 and of the water distribution assembly 110 is shown in partial section in FIG. 2.

FIG. 3 is a view in partial section sequentially following FIG. 2 illustrating the operation of the water distribution assembly 110 relative to the head 30 and the hand piece 20 and the burr 70.

FIG. 4 is a plan view of a portion of the water distribution system 110, taken generally along line 4—4 of FIG. 3. FIG. 4 comprises a plan view of the bottom of the water distribution assembly 110.

FIG. 5 is a top view of the hand piece 20 and the water distribution assembly 10 illustrating the movement of the water distribution assembly 110 relative to the head 30 and the hand piece 20.

Figure 6:
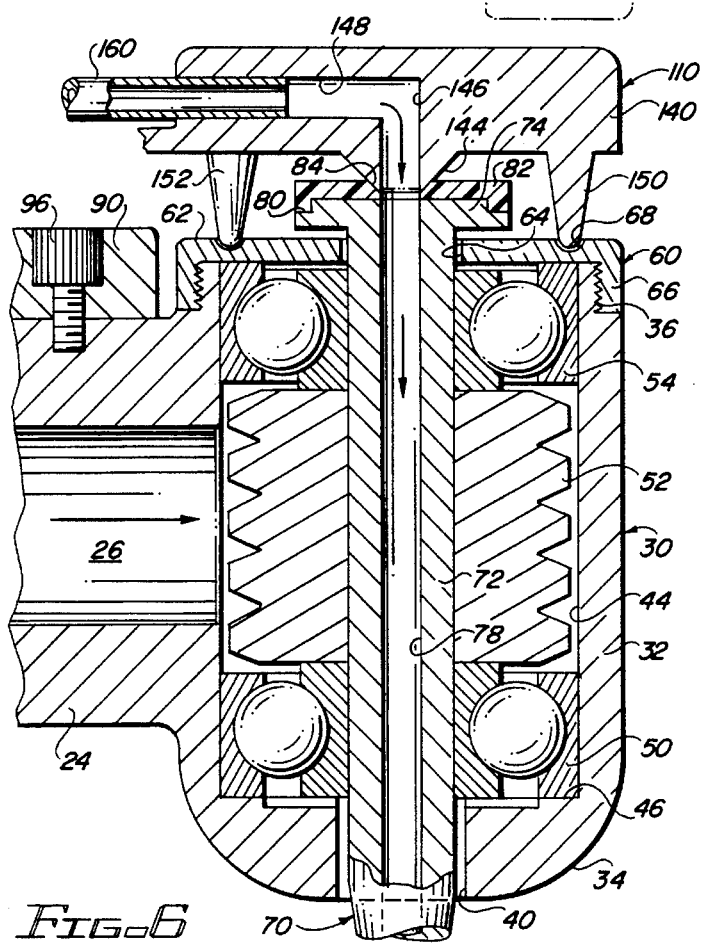
FIG. 6 is an enlarged view in partial section taken generally along line 6—6 of FIG. 1.

FIG. 6 is a view in partial section through the head 30 and a portion of the water distribution assembly 110, and illustrating the cooperative arrangement among the various elements in the head 30, the water distribution assembly 110, and the burr 70.

For the following discussion of the dental drill apparatus 10, reference will be made to FIGS. 1 through 6.

Within the handle 24 of the hand piece 20 is a bore 26. The bore 26 is shown in FIG. 6. The bore 26 extends to the head 30. The head 30 comprises generally a cylindrical housing 32 with a rounded or convex bottom 34. At the top of the cylindrical portion 32 are external threads 36. The external threads 36 cooperate with a cap 60, as will be discussed below.

Extending upwardly through the rounded or convex bottom 34 of the head 30 is a bottom central bore 40. The bore 40 extends to an internal bore 44 within the cylindrical portion 32 of the head 30. The internal bore 44 is substantially larger in diameter than is the bottom central bore 40. At the bottom of the internal bore 44 is a bottom step or shelf 46. The bottom step or shelf 46 comprises a seat for a lower bearing set 50. The bearing set 50 comprises a set of ball bearings which support the lower portion of a turbine 52. Above the turbine 52 within the bore 44 is a second bearing set, an upper bearing set 54.

The bore 44 is closed at the top portion of the cylinder 32 by the cap 60. The cap 60 includes a top 62 through which extends an aperture 64. Extending downwardly from the top 62 is an internally threaded bottom cylindrical portion 66. The internal threaded portion 66 receives or matingly engages the internally threaded top portion 36 of the cylinder 32.

On the top 62 of the cap 60 are three recesses 68. The recesses 68 receive alignment pins of the water distribution assembly 110, as will be discussed in detail below.

The burr 70 extends through the aperture 64 in the cap 60 and downwardly through the top bearing set 54, through the turbine 52, which includes an internal bore, through the bottom bearing set 50, and through the central bore 40. The burr 70 includes a central shank 72 which extends through the head 30, an outwardly extending head 74 at the top of the shank 72, and the bottom tip 76. A bore 78 extends through the burr 70, including through the head 74, the shank 72, and the tip 76.

The burr 70 also includes a step or shoulder 80 on the head 74. A cap 82 is disposed on the head 74 and seated against the step or shoulder 80. The cap 82 includes a hole or aperture 84 which communicates with the bore 78.

The cap 82 is made of a low friction material and may be replaced as it wears out. The wear is due to friction with a portion of the water distribution system 110, as will be discussed below.

The block 90 is disposed on the top of the handle 24 adjacent to the head 30. The block 90 includes a top surface 92 which is flat or generally planar. The block 90 is appropriately secured to the handle 24 by a pair of cap screws 94 and 96.

Between the cap screw 94 and 96 is a bottom bore 98, and coaxially disposed relative to the bottom bore 98 is a top bore 100. The top bore 100 has a diameter which is less than diameter of the bottom bore 98. The top bore 98 extends to the top surface 92.

Disposed within the bottom bore 98 is a base 102. Extending upwardly from the base 102 and extending through the top bore 100 and outwardly above the top surface 92 of the block 90 is a post 104. A hinge pin 106 extends through the post 104, as will be discussed below. There is a relatively loose fit between the base 102 and the bottom bore 98 and between the post 104 and the top bore 100 to allow the post 104, and the water distribution assembly 110, which is secured to the post 104 through the hinge pin 106, to pivot and move freely, as will be discussed below and as may best be understood from FIGS. 3 and 5.

The water or liquid distribution assembly 110 includes a rear thumb piece 112 which has a knurled top 114 and a bottom recess 116. Disposed within the bottom recess 116 is a compression spring 118. A ball 120 is disposed against the compression spring 118 and is appropriately pinned within the recess 116 to prevent the ball 120 from moving out of the recess 116. A portion of the ball 120 extends below the thumb piece 112, as best shown in FIG. 2. The compression spring 118 biases the ball downwardly against the top surface 92 of the block 90. Accordingly, the thumb piece 114 is biased upwardly, away from the block 92.

A bridge 130 extends between the thumb piece 112 and a block 140. The bridge 130 includes a slot 132 which receives the top or upper portion of the post 104 of the block 90. A pair of aligned bores communicate with the slot 132 through the bridge 130. The bores include a hinge pin bore 134 and a hinge pin bore 136. The hinge pin bores 134 and 136 are best shown in FIGS. 4 and 5. The hinge pin 106 extends into the aligned bores 134 and 136. The pin 106 accordingly defines a pivot pin on which the water distribution assembly 110 pivots relative to the block 90 and to the head 130 on the post 104.

The block 140 of the water distribution assembly 110 includes a generally flat bottom 142, with a central conical element 144 extending downwardly from the bottom 142. A bore 146 extends upwardly through the conical element 144 and through the block 140. The bore 146 extends to a radial bore 148. The bore 148 comprises a passageway which receives water or other appropriate liquid from a conduit 160.

Also extending downwardly from the bottom 142 are three alignment and spacer elements 150, 152, and 154. The elements 150, 152, and 154 extend into the recesses 68 on the top 62 of the cap 60. This is best shown in FIG. 6.

The conical element 144, or its tip, extends into the hole or aperture 84 of the cap 82 on the burr 70. Water, or whatever liquid is desired, accordingly flows from the conduit 160 through the bores or passageways 148 and 146 into the bore 78 of the burr 70.

Thus, the external water conduit 160 extends to the passageway 148 to provide a flow of water or saline solution to the conduit 148 and to the bore 78 of the burr 70, as best shown in FIG. 6.

With the spring 118 and the ball 120 providing an upward bias for the thumb piece 112, the block 140 is biased downwardly or pivoted downwardly through the pivot pin 106 extending through the bridge 130. The spacer or cushion elements 150, 152, and 154 provide a downward limit to the pivoting movement of the block 140. It will be noted that there is a space between the bottom surface 142 of the head block 140 and the top surface of the cap 60, as best shown in FIGS. 2 and 6.

With the conical element 144 of the block 140 disposed against and partially within the hole or aperture 84, liquid directed through the conduit 160 and the passageway 148 and bore 146 is directed to the bore 78 of the burr 70. The liquid then flows downwardly through the bore 78 and outwardly through the drilling tip 76.

Air flowing through the bore 26 of the hand piece 20 flows through the handle 24 and is directed against the blades of the turbine 52. The rotation of the turbine 52 in turn rotates the burr 70 for drilling purposes. This is best shown in FIG. 6.

Air escaping from the turbine 52 flows outwardly from the head 30, and a portion of the outwardly flowing or escaping air flows upwardly through the aperture 64 in the cap 60. The air flowing out of the aperture 64, and about the upper portion of the shank 72 by the head 74 of the burr 70, acts as a motive force for any water flowing from the conduit 148 and through the bores 146 and 144 that does not flow into the bore 78 of the burr 70. The outwardly flowing air acts as a slinger to move the water outwardly from the head 30, and accordingly outwardly away from the rotating elements within the head 30 and away from the burr 70.

When it is desired to change the burr 70, thumb pressure is placed on the thumb piece 114 to pivot the thumb piece 114 downwardly against the bias of the spring 118. The block 140 pivots upwardly, above the head 74 of the burr 70. This is shown in FIGS. 2 and 3.

When the block 140 clears the head 74 and the cap 82 of the burr 70, the assembly 110 is then pivoted or moved laterally, as shown in FIG. 5. With the assembly 110 pinned to the post 104, and with the post 104 loosely held within the block 90, the post 104 is able to rotate within the block 90 to allow for the lateral movement of the head piece 140 away from the head 74 of the burr 70, as shown in FIG. 5.

With the water distribution assembly 110 away from the burr 70, the burr is able to be changed or removed from the head 30. A new burr is then installed within the head 30.

The assembly 110 is then moved laterally back to its original position, with the head 30 and block 140 appropriately aligned, and the thumb pressure on the thumb piece 112 is released, allowing the biasing action of the spring 118 between the ball 120 and the thumb piece 112 to hold the block 140 downwardly against the cap 60 of the head 30. With the head of the new burr receiving the conical element or boss 144, water or other desired liquid will flow to and through the new burr 70 when the drill apparatus is operated.

Figure 6A:
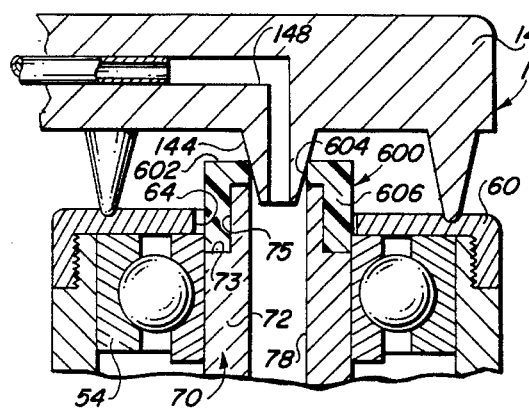
FIG. 6A comprises a view in partial section of an alternate embodiment of FIG. 6.

FIG. 6A comprises an enlarged view in partial section of a portion of the apparatus of FIG. 6, namely the upper portion of the head 30, with the cap 60 disposed thereon, and with the burr 70 extending through the head 30 and in contact with the water distribution assembly 110. In FIG. 6A, the water distribution assembly 110 is shown in generally the same configuration as illustrated in FIG. 6. However, the upper portion of the burr 70 is slightly altered or modified from that shown in FIG. 6.

The burr 70 includes an upper shoulder 73 in place of the outwardly extending head 74 of FIG. 6. The shoulder 73 extends to a reduced diameter portion 75 which extends generally upwardly from the shoulder 73 and is generally a cylindrical configuration, as is the shank 72.

Disposed on the shoulder 73, and about the reduced diameter cylindrical portion 75, is a burr cap 600. The burr cap 600 includes a top portion 602 which is disposed on the top of the shank 72. A hole or aperture 604 extends through the top 602 and is aligned with the bore 78 in the shank 72 of the burr 70. A cylindrical skirt 606 extends downwardly from the top 602 and is disposed on the shoulder 73. The outer diameter of the burr cap 600 is substantially the same as the outer diameter of the shank 72 of the burr 70.

The burr cap 600 is preferably made of low friction material, such as a polytetrafluoroethylene product made under the DuPont "Teflon" trademark.

The tapered conical portion 144 of the block 140 extends into the aperture 604 for transporting water through the conduit or passageway 148 to the bore 78 of the burr 70.

As the frictional engagement between the conical tapered element 144 and the burr cap 600 wears, the burr cap 600 may be easily replaced.

Figure 6C:
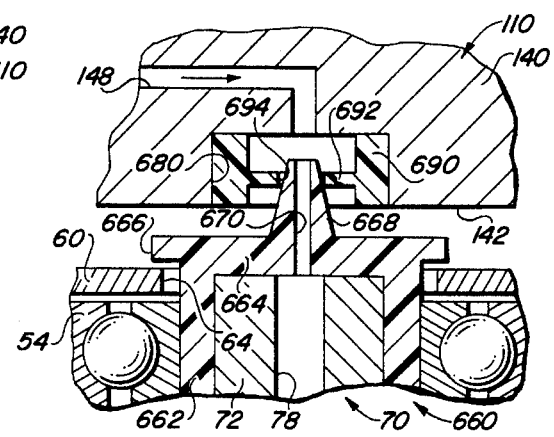
FIG. 6C comprises a view in partial section of still another embodiment of the apparatus of a portion of the apparatus of FIG. 6.
Figure 6B:
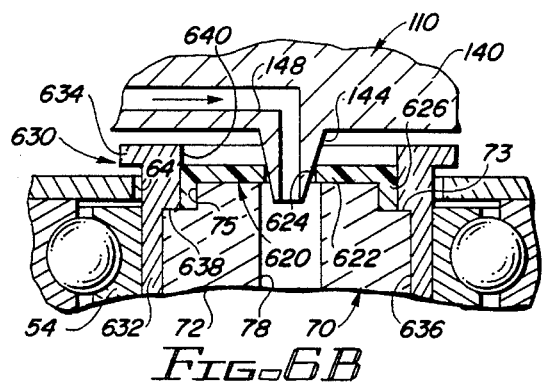
FIG. 6B comprises an enlarged view in partial section of another alternate embodiment of a portion of the apparatus of FIG. 6.

Another variation or embodiment of the burr 70 from that illustrated from that in FIG. 6A is shown in FIG. 6B. FIG. 6B comprises an enlarged view in partial section of the upper portion of the burr 70 and the water distribution assembly 110 relative to the head 30.

On the shoulder 73 is disposed a cap 620, but the cap 620 is smaller than the cap 600 of FIG. 6A. Moreover, the shoulder 73 is somewhat wider, and the upper reduced diameter cylindrical portion 75 is shorter. The cap 620 includes a top 622 with an aperture 624 extending therethrough. The cap 620 also includes a shortened skirt 626 which extends downwardly from the top 22 and is disposed on the shoulder 73.

The outer diameter of the skirt 626 is less than the outer diameter of the shank 72, and is accordingly less than the width of the shoulder 73.

An outer bearing sleeve 630 is disposed about the shank 72 of the burr 70 and extends upwardly above the cap 620. The aperture 64 in the cap 60 of the head 30 is somewhat larger than that illustrated in FIGS. 6 and 6A so as to accommodate the extra diameter of the outer bearing sleeve 630.

The outer bearing sleeve 630 includes a downwardly extending cylindrical portion 632 which is in contact with the bearing assembly 54. The upper portion of the cylindrical portion 632 extends through the aperture 64 and the cap 60. Above the cap 60 the outer bearing sleeve 630 includes an outwardly extending flange portion 634.

The sleeve 630 includes an inner bore 636 which is disposed about the shank 72. The sleeve 630 also includes an upper bore 640 which extends about the cap 620. Between the lower bore 636 and the upper bore 640 is a shoulder 638. The shoulder 638 is disposed on an outer portion of the shoulder 73 of the burr 70, radially outwardly from the skirt 626 of the cap 620.

The tapered conical portion 144 of the water distribution element 110 extends into the aperture 624 of the cap 620. Thus, water flows through the conduit 148 and into the bore 78 of the burr 70.

Again, the cap 620 is preferably made of low frictional material so as to minimize the wear between the cap 620 and the tapered conical portion 144 of the block 140. The sleeve 632 helps to hold the cap 620 in place and offers a separate element of protection to prevent water from getting into the bearing assembly 54. Any water which leaks out from the burr 70 is pushed away by air from the turbine 52 in all of the alternate embodiments of the apparatus illustrated in FIGS. 6, 6A, 6B, 6C, 6D, etc.

FIG. 6C comprises another alternate embodiment of the apparatus illustrated in FIG. 6, with modifications made to both the burr 60 and the block 140.

In the embodiment of FIG. 6C, the shank 72 of the burr 70 is of a general cylindrical configuration at its upper portion. The bore 78 extends through the shank 72 and communicates directly with a bore 670 in a sleeve 660. The sleeve 660 includes a cylindrical skirt 662 which is disposed about the upper portion of the shank 72 and is contact with the bearing set 54.

The sleeve 660 includes a top wall 664 which is disposed on the top of the shank 72. The cylindrical portion 662 extends above the cap 660 and through the aperture or hole 64 in the cap 60. Between the cap 60 and the block 140 is an outwardly extending flange portion 666.

A conically tapered element 668 extends upwardly from the cap 664 and is aligned with the bore 78. The bore 670 extends through the conically tapered element 668 to provide communication between the bore 78 of the burr 70 and water flowing in the conduit 148 in the block 140 of the water distribution assembly 110.

In the water distribution assembly 110, in place of the conical tapered element 144, there is a bore 680. The bore 680 extends into the block 140 and upwardly from the bottom surface 142 thereof. The bore 680 is aligned with the burr 70, and accordingly with the upwardly extending conically tapered portion 668 of the sleeve 660.

A bushing 690 is disposed in the bore 680. The bushing 690 comprises a generally circular element, the outer diameter of which is substantially the same as the inner diameter of the bore 680. A central web 692 comprises a central wall in the bushing 690. An aperture 694 extends through the central web 690. The tapered conical portion 668 extends through the aperture 694. Contact between the bore 694 and the tapered conical element 668 provides a seal for the flow of fluid (water) from the conduit 148 and into the bore 670 of the sleeve 660. The fluid (water) then flows from the bore 670 into the bore 78 of the burr 70.

Figure 6D:
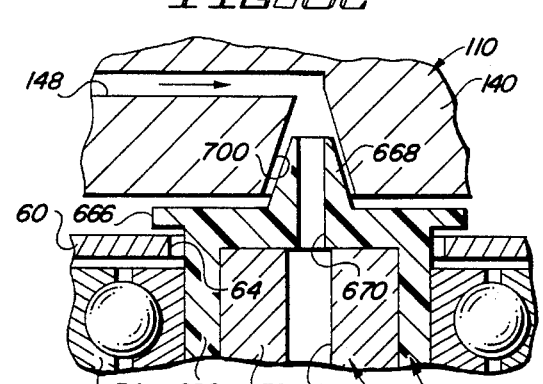
FIG. 6D comprises an enlarged view in partial section of yet another alternate embodiment of a portion of the apparatus of FIG. 6.

FIG. 6D comprises an enlarged view in partial section of another alternate embodiment of the apparatus of FIG. 6, and specifically an alternate embodiment of the element shown in FIG. 6C. The burr 70, with its sleeve 660, is substantially the same in the embodiment of FIG. 6D as shown in FIG. 6C. However, the block 140 of the water distribution assembly 110 is slightly different from that shown in FIG. 6C.

Rather than the generally cylindrical bore 680 extending into the block 140, as shown in FIG. 6C, a tapered bore 700 extends into the block 700 to communicate with the conduit 148. The tapered bore 700 contacts or matingly engages the conically tapered elements 668 of the sleeve 660 to provide a sealing engagement between the sleeves 660 and accordingly between the burr 70, and the block 140 of the water distribution assembly 110. The water then flows from the conduit 148 into the bore 670 of the sleeve 660 and into the bore 78 of the burr 70. Again, the sleeve 660 is made of relatively low friction material so as to minimize the wear between the conically tapered bore 700 and the conically tapered element 668 of the sleeve 660.

For purposes of clarity, a spaced relationship is shown between the bore 700 and the conical element 668. Different angles may be used on the two elements to minimize frictional contact, if desirable.

As with the apparatus 10 of FIGS. 1–6, the air from the turbine (not shown), which rotates the burr 70, escapes through the apertures 64 in the embodiments of FIGS. 6A, 6B, 6C, and 6D, and acts as a slinger to sling away any water (liquid) that escapes from the water distribution assembly 110 and the caps of the burr 70. This prevents the water from getting into the head of the handpiece and then into the turbine elements, bearings, etc.

FIG. 7 is a view in partial section of a portion of an alternate embodiment dental drill apparatus 210. The drill apparatus 210 is for a relatively low speed, belt or air driven hand drill.

The relatively low speed dental drill apparatus 210 includes a hand piece 220 which includes an inner cylinder 222 through which extends a bore 224. An outer cylindrical handle portion 226 is disposed about the inner cylinder 222. The outer cylindrical element 226 includes a radially outwardly extending flange 228 which is a portion of a cylindrical housing 230. Remote from the radial flange 228 is an inwardly extending radial flange 232. An opening 234 extends through the radial flange 232.

A pulley 250 is disposed at the outer end of the hand piece 220, and the pulley 250 is in turn secured to an externally threaded shaft 240. The shaft 240 includes a longitudinally extending bore 242 through which the water, etc., flows to a hollow burr (not shown) which is appropriately secured to the distal end of the shaft 240.

The pulley 250 includes an outer groove 252, and a hub 254. The hub 254 includes a bore 256. A drive belt 258 is shown disposed in the outer groove 252 of the pulley 250.

A portion of the hub 254, of the pulley 250 is disposed within the housing 230.

The shaft 240 is secured to the pulley 250 through a center fastener element 260. The element 260 includes a cylindrical portion 262 which is appropriately secured, as by a press fit, or the like, within the bore 256 of the pulley 250. The element 260 includes an internally threaded bore 264 through which extends the shaft 240. The shaft 240, as indicated above, is externally threaded, and the shaft 240 extends through the internally threaded bore 264 of the element 260.

Figure 9:
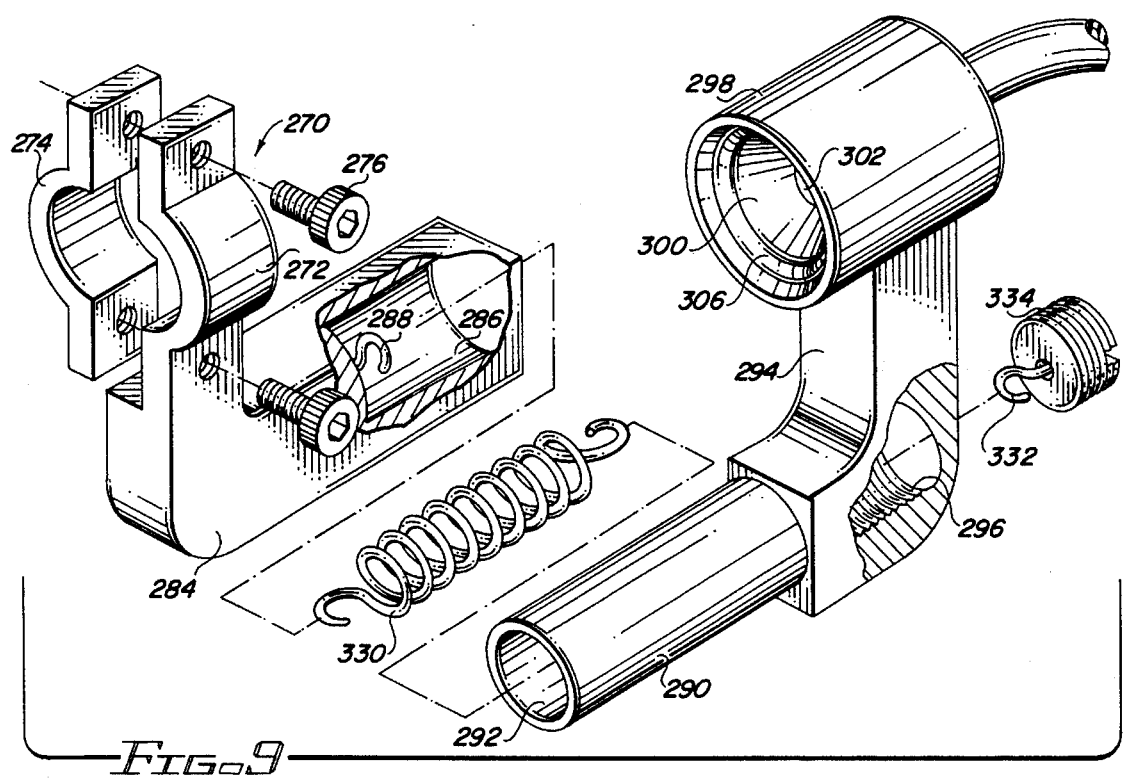
FIG. 9 is an exploded perspective view of the apparatus of FIG. 7.

The outer end of the shaft 240 extends from the pulley 250 into a water or liquid distribution assembly 270. FIG. 8 is a side view in partial section through a portion of the water distribution assembly 270, and FIG. 9 is an exploded perspective view of the water distribution assembly 270. For the following discussion, reference will be made to FIGS. 7, 8, and 9.

The water distribution assembly 270 includes an arm 272 which extends outwardly to another arm 284. The arm 270, as best shown in FIG. 9, includes a concave portion which is disposed about the outer cylinder 226 of the hand piece 220. The arm 270 is secured to the hand piece 220 by a bracket 274. The bracket 274 also includes a concave portion, essentially the mirror image of the concave portion of the arm 272, to receive the outer cylinder 226. The bracket and the arm are appropriately secured together by a pair of screws 276. The concave portions of the arm 272 and the bracket 274 fit over the hand piece 220. The arm 272 and the bracket 274 comprise a clamp to secure the water distribution assembly 272 to the hand piece 220.

The arm 272 extends from the arm 284. The arm 284 is substantially perpendicular to the arm 272, and the arm 284 is accordingly generally parallel to the hand piece 220.

The arm 284 includes a bore 286 remote from the arm 272. At the bottom of the bore 286 is an anchor pin 288. A sleeve is movably disposed within the bore 286. The sleeve 290 includes a bore 292. The bores 286 and 292 are aligned with each other, as best shown in FIGS. 7 and 8.

An arm 294 extends outwardly generally perpendicularly to the sleeve 290. The arm 294 is generally parallel to the arm 272.

A threaded bore 296 extends through the arm 294 and communicates with the bore 292 in the sleeve 290.

At the distal end of the arm 294, remote from the bore 296 and from the sleeve 290, is a block 298. The block 298 includes a conical bore 300 in which are two O-ring grooves, including an O-ring groove 302 and an O-ring groove 306.

A pair of O-rings, including an O-ring 304 and an O-ring 308, are disposed in the grooves 302 and 306, respectively. Since the bore 300 is conical, the diameters of the O-ring grooves 302 and 306 differ, as do, of course, the diameters of the O-rings 304 and 308.

Coaxially aligned with the conical bore 300 is a bore 310. The bore 310 extends through the block 298 to communicate with the bore 300.

A conduit 314 extends through the bore 310 and outwardly therefrom, and terminates slightly outwardly from the block 298. A flexible conduit 316 is appropriately secured to the portion of the conduit 314 outside of, or outwardly from, the block 298. The conduit 316, and the conduit 314, are used to transport a flow of liquid, such as sterile water, or saline solution, etc., to the liquid distribution assembly 270.

Disposed within the bore 300 is a seal cone 320. The seal cone 320 includes two O-ring grooves, including an O-ring groove 322 and an O-ring groove 326. The O-ring groove 322 is complementary to the O-ring groove 302, and the O-ring groove 326 is complimentary to the O-ring groove 306. Accordingly, the O-ring groove 322 receives a portion of the O-ring 304, while the O-ring groove 326 receives a portion of the O-ring 308. This is best shown in FIG. 7. The O-ring grooves 322 and 326 are best shown in FIG. 8.

The two conical elements, the conical bore 300 and the conical seal cone 320, with their O-rings and grooves, comprise seal elements for cooperatively sealing the burr (not shown) and the liquid distribution system 270 as the burr and its associated elements rotate.

Extending through the seal cone 320 is a threaded bore 328. The threaded bore 328 is coaxially aligned with the threaded bore 264 of the center element 260. The externally threaded shaft 240 extends through the bore 224 of the cylinder 222 of the hand piece 220 and into the bore 264 of the center element 260, and into the bore 328 of the seal cone 320. Accordingly, rotation of the pulley 250 by the belt 258 causes rotation of the element 260, and accordingly rotation of the shaft 240 and of the seal cone 320.

Within the element 240 is a bore 242. The bore 242 is appropriately aligned with the conduit 314 and the conduit 316 and receives a flow of liquid therefrom. The seal cone 320, with the O-rings 304 and 308, provide a seal to prevent water or other liquid from the conduits 314 and 316 from escaping from the block 298 and from the hand piece 220.

The arm 284 comprises an anchor element to which the block 298 is secured through the arm 294 and the sleeve 290. Tension between the block 298 and the seal cone 320 is provided through the arm 294 and the sleeve 290 relative to the arm 284.

As indicated above, an anchor pin 288 is disposed at the bottom of the bore 286. A tension spring 330 is secured to the anchor pin 288 and is disposed in the bore 292 of the sleeve 290.

The end of the spring 330 remote from the anchor pin 288 is secured to an anchor pin 332 which is in turn secured to a tension adjusting screw 334. The tension adjusting screw 334 is movable within the threaded bore 296. Rotation of the screw 334 causes tension to increase or decrease through the tension spring 330, the arm 294, and the block 298, relative to the seal cone 320 and its sealing elements, the O-rings 304 and 308.

In FIG. 8, the arm 284 and the block 298 are shown pulled away from the seal cone 320.

An outward pull on the arm 284, as indicated by the relatively large arrow thereon, allows the block 298 to be pulled away from the seal cone 320. The sleeve 290 essentially acts as a pivot pin to allow the block 298, and the arm 294 to be pivoted away from the seal cone 320, as desired.

An alternate embodiment of the tension screw 330 and its associated elements is illustrated in FIG. 10. FIG. 10 comprises a view in partial section through a portion of an alternate embodiment water distribution assembly 370.

A portion of an arm 372, which corresponds to the arm 272 of the water distribution assembly 270 of FIG. 7 and 8, is illustrated. The arm 372 is connected to an arm 384, which corresponds to the arm 284 of the water distribution assembly 270. The arm 384 includes a bore 386, with a threaded bore 388 extending into the arm 384 from the end of the bore 386.

A cylindrical pin 390 extends into the bore 386. The pin 390 includes an internally threaded bore 392 which is coaxially aligned with the threaded bore 388. The pin 390 also includes a shoulder 394 which limits the movement of the pin into the bore 386.

The pin 390 extends to an arm 400, which corresponds to the arm 294 of the water distribution assembly 270. The threaded bore 392 extends through the arm 400 and receives a screw 410. The screw 410 includes a screw head 412. A lock nut 414 is disposed about the screw between the arm 400 and the screw head 412. The screw 410 extends through the threaded bore 392 and into the threaded bore 388 of the block 384.

With the arm 384 fixed, rotation of the screw 410 by its head 412 will result in a movement of the arm 400 towards and away from the arm 384, as indicated by the double headed arrow in FIG. 10. When the appropriate tension between a block secured to the arm 400, not shown, but corresponding to the block 298, is achieved with respect to a seal cone, such as the seal cone 320 of FIG. 7, by rotation of the screw 410, the lock nut 414 may be tightened against the arm 400.

Figure 11:
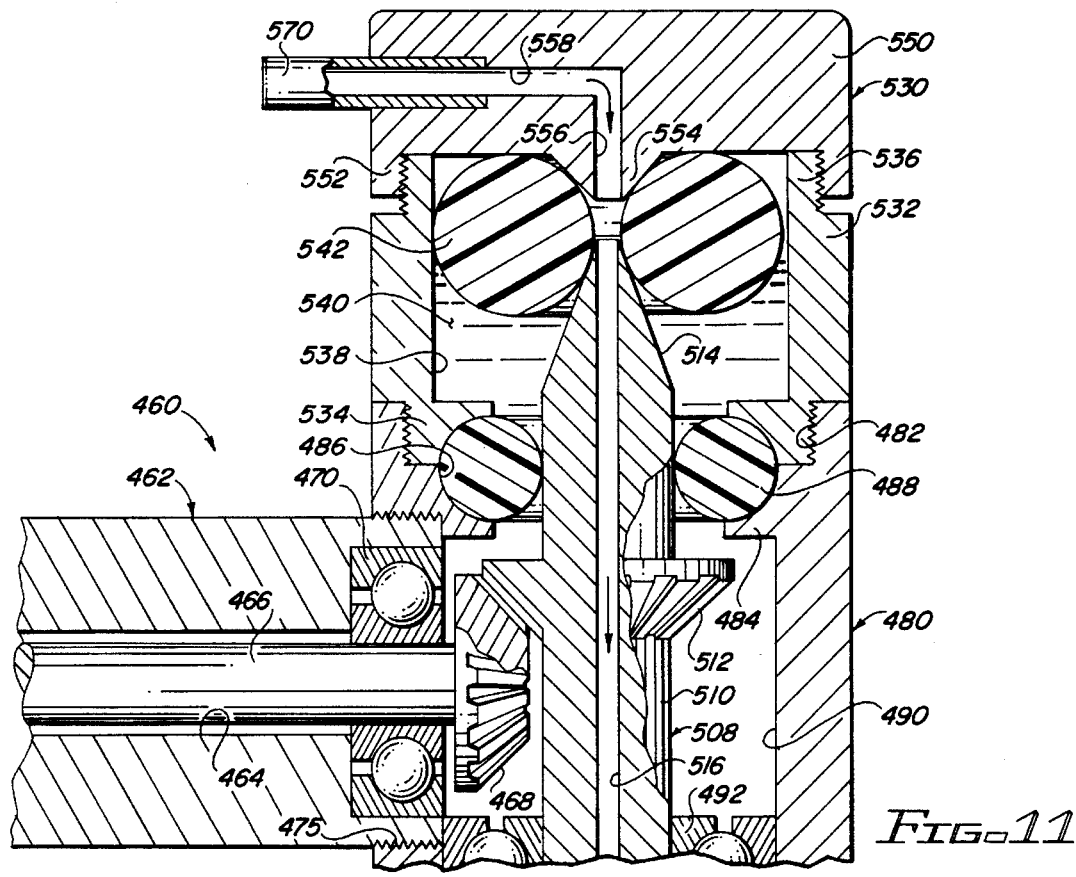
FIG. 11 is a view in partial section of another alternate embodiment of the apparatus of the present invention.

A water distribution assembly for a mechanically rotated dental drill is illustrated in FIG. 11.

FIG. 11 comprises a view in partial section of a portion of an alternate embodiment 460 of dental drill apparatus. The portion of the drill apparatus 460 illustrated in FIG. 11 includes a portion of a hand piece 462 and a portion of a head 480. The hand piece 462 includes a bore 464 through which extends a drive shaft 466. At the end of the drive shaft 466 disposed within the head 480 is a bevel gear 468. The bevel gear 468 is supported at the head 480 by a bearing set 470. The shaft 466 extends, ultimately, to a drive motor, not shown.

The hand piece 462 is appropriately secured to the head 480 through a threaded engagement 475.

The head 480, insofar as the present invention is concerned, includes a top, internally threaded, bore 482, with a radially inwardly extending flange 484 disposed at the lower end of the bore 482. The radially inwardly extending flange 484 includes an O-ring groove 486 in which is disposed an O-ring 488.

The head 480 also includes a bore 490 below the flange 484. A bearing set 492 is disposed in the bore 490, spaced apart a predetermined distance below the flange 484.

The bearing set 492 helps to support a burr 508, which includes a shaft or shank 510. A bevel gear 512 is disposed on the shank 510 and matingly engages the bevel gear 468 of the drive shaft 466.

The shank 510 includes a conical top 514 which extends upwardly above the O-ring seal 488, and accordingly above the head 480 and into a liquid delivery or distribution assembly 530.

Within the shank 510 is an axially extending bore 516. Water is delivered by the liquid delivery or distribution assembly 530 to the axial bore 516 and the liquid then flows downwardly through the bore 516 and to the tip (not shown) of the burr 508.

The liquid delivery assembly 530 includes a relatively short cylindrical block 532. The block 532 includes an externally threaded bottom boss 534 which matingly engages the internally threaded bore 482 of the head 480. The block 532 also includes an externally threaded top boss 536. Within the block 532 is a bore 538. The conical top portion 514 of the burr 510 extends to and is disposed within the bore 538 of the block 532.

The bore 538 about the upper or top portion of the burr 510 is filled with a relatively heavy oil 540. The top of the bore 538, above the oil 540, and about the upper portion of the conical top 514 is closed and sealed by an O-ring 542. The O-ring 542, and the O-ring 488, may both be made of teflon, or the like, to allow the burr 510 to rotate easily and smoothly. The O-rings 488 and 542 provide a seal against the burr shank 510 to prevent the oil 540 from leaking downwardly along the burr shank 510 and outwardly from the block 532. The seals 488 and 542 also prevent the delivered liquid from leaking outwardly. Essentially, the top O-ring 542 confines water within the block 532 and allows the liquid to flow only into the bore 516 of the burr shank 510.

The block 532 is closed by a cap 550. The cap 550 includes an internally threaded rim 552 which matingly engages the externally threaded boss 536 of the block 532. The cap 550 includes a central conical boss 554 which extends downwardly from the cap 550 and into the bore 538. The conical boss 554 comprises an inverted cone which bears against the seal 542. Accordingly, the conical boss 554 comprises a sealing element which cooperates with the seal element 542 and the conical top 514 of the shank 510 to seal the upper portion of the shank 510 and the block 532.

Extending through the boss 554 is an axially extending bore 556. The bore 556 extends to and communicates with a radially extending bore 558.

A water conduit 570 is disposed in the bore 558. The conduit 570 provides a flow of water or other appropriate or desired liquid to the bore 558 and the bore 556 into the interior of the bore 538 of the block 532 and to the bore 516 of the burr shank 510. As will be noted from FIG. 11, the portion of the bore 538 to which the liquid from the bore 556 is subjected is a relatively small area and there is a relatively short distance between the bore 556 and the bore 516 of the burr shank 510.

The cap 550, or the bottom surface thereof, including the boss 554, seals against the O-ring 542. The O-ring 542 is in turn sealed against the top portion of the conical top 514 of the burr shank 510. As indicated above, the Oil 540 is confined about the upper portion of the burr 510 between the seals 488 and 542. Liquid accordingly is directed downwardly through the bore 516 and to the distal or bottom tip (not shown) of the burr 508 for cooling purposes.

As will be understood, the drill apparatus 460 is a relatively slow speed apparatus since it is a direct mechanical linkage drive system. The bore 516 in the burr 510 allows the cooling liquid to be transported from an external source (not shown) to the burr 508, and through the burr to its tip (not shown).

Figure 12:
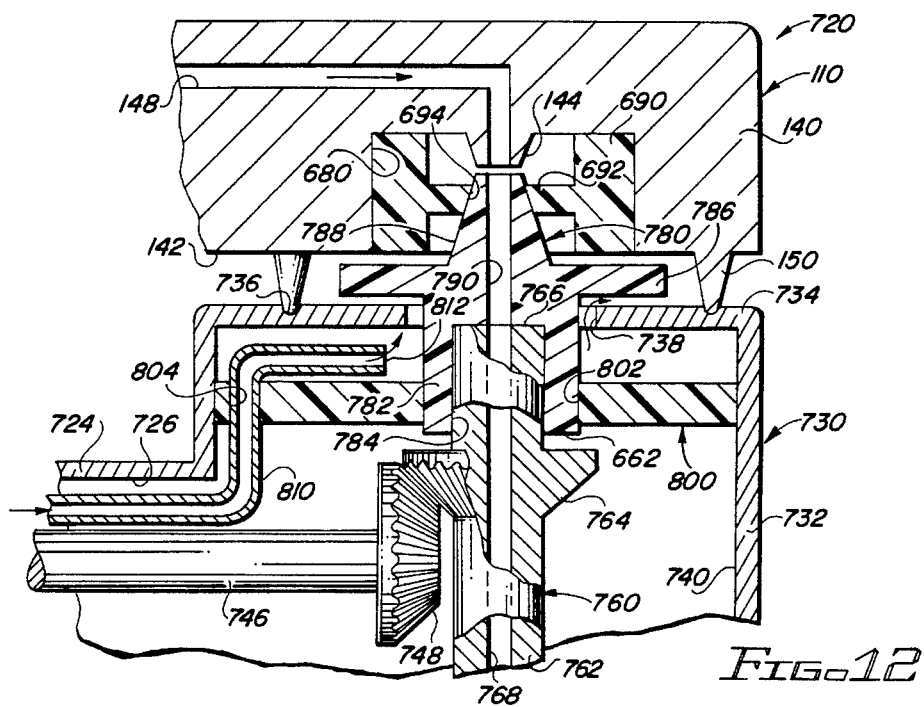
FIG. 12 is a view in partial section of an alternate embodiment of the apparatus of FIG. 11.

FIG. 12 comprises a view in partial section of an alternate embodiment of the low speed drill apparatus of FIG. 11, but utilizing a the water distribution assembly 110 of FIGS. 1–6, etc., with a modification. FIG. 12 comprises a representation of the upper portion of apparatus 720 which includes a handle 724 through which extends a bore 726 and which extends to a head 730. The head 730 includes a generally cylindrical element 732 which is closed by a top 734. Extending downwardly into the top 734 are recesses 736 which receive elements 150 which extend downwardly below the bottom 142 of the water distribution assembly 110, discussed in detail above.

Extending through the top 734 of the head 730 is an aperture 738.

The water distribution assembly 110 includes the modification best illustrated in FIG. 6C, and discussed above in conjunction therewith. The modification includes a bore 680 which extends upwardly into the head or block 140, and in which bore 680 is disposed a bushing 690. The conical element 144 extends downwardly into the bore 680 from the head or block 140 and terminates above a central web 692 through which extends an aperture 694.

Extending through the bore 726 of the handle 724 is a drive shaft 746. On the outer end of the shaft 746 is a bevel gear 748. The bevel gear 748 meshes with a bevel gear 764 on a shank or shaft 762 of a burr 760. The burr 760 is disposed within the bore 740 of the cylindrical element 732 of the head 730.

The burr 760 includes a generally flat top 766 above the bevel gear 764. A cap element 780 is disposed on the top 766 of the burr 760.

The cap element 780 includes a generally cylindrical or skirt portion 782 which extends downwardly over the top portion of the shaft or shank 762 above the bevel gear 764. The cylindrical portion 782 extends through the aperture or hole 738 in the top 734.

Within the cylindrical portion 782 is a bore 784. The upper portion of the shaft 762 above the gear 764 is disposed in the bore 784 of the cap 780.

Above the top 734 is a radially outwardly extending flange 786 on the cap element 780. The flange 786 extends radially outwardly from the cylindrical portion 782.

Extending upwardly from the flange 786 is a conical element 788. The conical element 788 extends into the aperture 694 in the central web 692 of the bushing 690.

A bore 790 extends axially through the conical element 788 and the cylindrical portion 782 to communicate with the bore 768 in the shaft 762 of the burr 760. Water accordingly flows through the water distribution assembly 110 in the passageway or conduit 148, and to the bore 790, and from the bore 790 to the bore 768, and from the bore 768 outwardly through the tip (not shown) of the burr 760.

Both the cap element 780 and the bushing 690 are of low frictional material, so as to minimize the frictional and sealing engagement between the conical portion 788 of the cap 780 and the bushing 690. This is, of course, as discussed above in conjunction with the other embodiments discussed previously.

Also disposed in the bore 740, and located above the meshing gears 748 and 764, is a bushing 800. The bushing 800 includes two apertures, an aperture 802 through which extends the cylindrical or skirt portion 782 of the cap 780, and a bore 804 through which extends a portion of an air conduit 810. The air conduit 810 also extends through the bore 726 of the handle 724.

The air conduit 810 includes an outer tip or distal end 812 which is disposed above the bushing 800, or between the bushing 800 and the top 734 of the head 730. The tip or end 812 is disposed adjacent to the aperture 738. The purpose of the air conduit 810, and the location of its outer end or tip 812, is to provide a source of compressed air to insure that any water leaking from the water distribution system 110 and the burr 760, with respect to the bushing 690 and the cap 780, is slung outwardly in the space between the bottom surface 142 of the block 140 and the top 734 of the head 730. The air slinging the water outwardly insures that the water does not migrate downwardly into the head 730 and into the gear elements 748 and 764.

Again, the bushing 800 is preferably made of low friction material so as to minimize the wear between the bushing 800 and the cap 780, or its cylindrical skirt 782, as the burr 760 is rotated.

Thus, it will be noted that the general concept of the present invention, namely water distribution through a burr, is feasible with both low speed hand pieces, as illustrated in FIGS. 11 and 12, as with high speed hand pieces, as illustrated in FIGS. 1–10, and as discussed in conjunction with the respective figures.

It will be noted that advances in the dental arts change configurations and material of burrs and related elements. Ceramic burrs, because of their smoothness, are advantageously currently used with high speed drills. "Teflon" brand of polytetrafluoroethylene material coatings and materials are also currently used for reducing friction in rotating and movable elements. The apparatus of the present invention obviously may use any or all of such contemporary materials and new materials as they are developed.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Dental drill apparatus comprising in combination:

a handpiece;

a head connected to the handpiece;

a burr, including a shank rotatably secured to the head and extending outwardly therefrom;

a bore extending through the burr for conveying a cooling liquid from the head;

a liquid distribution system connected to the head for providing liquid to the bore of the burr, including
   a block disposed adjacent to the head and the burr removable relative to the head for changing the burr, and a liquid delivery bore in the block through which the cooling liquid flows to the bore in the burr; and means for sealing the block and the burr, including a conical element on the block.

2. The apparatus of claim 1 in which the burr includes a cap having an aperture communicating with the bore in the burr.

3. The apparatus of claim 2 in which the conical element extends downwardly from the block.

4. The apparatus of claim 3 in which the element extends into the aperture in the cap.

5. The apparatus of claim 1 in which the conical element comprises a conical bore extending into the block.

6. The apparatus of claim 5 in which the burr includes a seal cone which extends into the conical bore.

7. The apparatus of claim 1 in which the block includes a bore and a seal element disposed in the bore, and the conical element comprises a conical element disposed against the seal element.

8. The apparatus of claim 7 in which the burr includes a conical top extending into the bore in the block and disposed against the seal element.

9. The apparatus of claim 1 in which the block is pivotally secured to the head.

10. The apparatus of claim 9 in which the block is spring biased against the head and the burr.

11. The apparatus of claim 10 in which the block pivots on a post secured to the head.

12. The apparatus of claim 11 which further includes a bridge connected to the block and a thumb piece connected to the bridge remote from the block, and the block pivots on the post.

13. The apparatus of claim 12 in which the block includes a pin extending through the post and the bridge for pivoting the block.

14. The apparatus of claim 13 which further includes a compression spring disposed against the thumb piece to bias the block against the head and the burr.

15. The apparatus of claim 10 in which the block pivots on an arm secured to the head.

16. The apparatus of claim 15 in which the arm includes a tension spring for biasing the block against the head and the burr.

17. Dental drill apparatus comprising in combination:

a handpiece;

a head connected to the handpiece;

a burr rotatably connected to the head;

a bore extending through the burr for receiving a cooling liquid;

a liquid distribution assembly for providing a flow of liquid to the bore in the burr, including
    a block connected to a source of liquid, and
    bore means in the block communicating with the source of liquid and with the bore in the burr for transmitting the liquid to the burr; and means for pivoting the liquid distribution assembly away from the head and the burr for changing the burr.

18. The apparatus of claim 17 which further includes means for sealing the block and the burr.

19. The apparatus of claim 18 in which the means for sealing the block and the burr includes a conical element on the block.

20. The apparatus of claim 19 in which the conical element comprises a conical boss extending from the block to the burr.

21. The apparatus of claim 19 in which the conical element comprises a conical bore extending into the block.

22. The apparatus of claim 21 which further includes a seal cone secured to the burr and extending into the conical bore.

23. The apparatus of claim 17 in which the burr includes
a cap,
an aperture in the cap communicating with the bore in the burr, and
the liquid distribution assembly includes a conical element disposed in the aperture in the cap through which the liquid flows to the bore in the burr.

24. The apparatus of claim 17 in which the liquid distribution assembly further includes
a bottom surface on the block,
a bore in the block extending upwardly from the bottom surface and communicating with the bore means for transmitting the liquid to the burr,
a bushing in the bore in the block, and
an aperture in the bushing; and the burr includes
a cap,
a conical element extending upwardly on the cap and into the aperture in the bushing, and
a bore in the conical element and cap communicating with the bore in the burr through which the liquid flows from the liquid distribution assembly.

25. The apparatus of claim 24 which further includes a source of compressed air adjacent to the cap on the burr for slinging away from the burr any liquid leaking from the bushing and the cap.

26. The apparatus of claim 17 in which the liquid distribution assembly further includes
a bottom surface on the block, and
a conical bore extending into the block from the bottom surface and communicating with the bore means for receiving the liquid; and the burr includes
a cap,
a conical element extending upwardly on the cap and into the conical bore of the liquid distribution assembly, and
a bore in the conical element and cap communicating with the bore in the burr through which the liquid flows from the liquid distribution assembly to the burr.

27. The apparatus of claim 17 which includes a source of compressed air for slinging away from the head any liquid which may leak from the water distribution assembly and burr.

* * * * *